(12) United States Patent
Lian

(10) Patent No.: US 9,095,439 B2
(45) Date of Patent: Aug. 4, 2015

(54) CANNULATED MODULAR TIBIAL STEM COMPONENT PIECES FOR USE IN TOTAL ANKLE ARTHROPLASTY AND SYSTEMS FOR INSTALLING AND REMOVING SAME

(71) Applicant: George John Lian, Sacramento, CA (US)

(72) Inventor: George John Lian, Sacramento, CA (US)

( * ) Notice: Subject to any disclaimer, the term of this patent is extended or adjusted under 35 U.S.C. 154(b) by 58 days.

(21) Appl. No.: 14/190,014

(22) Filed: Feb. 25, 2014

(65) Prior Publication Data

US 2014/0180426 A1 Jun. 26, 2014

Related U.S. Application Data

(63) Continuation-in-part of application No. 13/573,887, filed on Oct. 12, 2012, which is a continuation-in-part of application No. 13/068,290, filed on May 6, 2011, now Pat. No. 8,475,463, which is a continuation-in-part of application No. 12/798,417, filed on Apr. 2, 2010, now Pat. No. 8,337,503.

(60) Provisional application No. 61/851,123, filed on Mar. 4, 2013, provisional application No. 61/821,681, filed on May 9, 2013, provisional application No. 61/212,533, filed on Apr. 13, 2009, provisional application No. 61/270,203, filed on Jul. 6, 2009.

(51) Int. Cl.
| | |
|---|---|
| *A61F 2/42* | (2006.01) |
| *A61B 17/88* | (2006.01) |
| *A61B 17/92* | (2006.01) |
| *A61F 2/46* | (2006.01) |
| *A61B 17/16* | (2006.01) |
| *A61B 17/17* | (2006.01) |
| *A61F 2/30* | (2006.01) |

(52) U.S. Cl.
CPC .......... *A61F 2/4202* (2013.01); *A61B 17/1604* (2013.01); *A61B 17/1637* (2013.01); *A61B 17/1682* (2013.01); *A61B 17/1739* (2013.01); *A61B 17/88* (2013.01); *A61B 17/92* (2013.01); *A61F 2/4603* (2013.01); *A61F 2/4606* (2013.01); *A61B 2017/1775* (2013.01); *A61F 2002/30329* (2013.01); *A61F 2002/30331* (2013.01); *A61F 2002/30387* (2013.01); *A61F 2002/30599* (2013.01); *A61F 2002/30616* (2013.01); *A61F 2002/4205* (2013.01); *A61F 2002/4619* (2013.01)

(58) Field of Classification Search
CPC .................. A61B 17/1682; A61B 2017/1775; A61B 17/88; A61B 17/92; A61F 2002/30329; A61F 2002/30331; A61F 2002/30387; A61F 2002/30599; A61F 2002/30616; A61F 2/4202; A61F 2002/4205; A61F 2/4603; A61F 2/4606; A61F 2002/4619
See application file for complete search history.

(56) References Cited

U.S. PATENT DOCUMENTS

| | | | | |
|---|---|---|---|---|
| 2005/0288792 | A1* | 12/2005 | Landes et al. | 623/21.18 |
| 2006/0229730 | A1* | 10/2006 | Railey et al. | 623/21.18 |

* cited by examiner

*Primary Examiner* — Larry E Waggle, Jr.
(74) *Attorney, Agent, or Firm* — Dennis A. DeBoo; Audrey A. Millemann; Weintraub Tobin

(57) ABSTRACT

An ankle replacement prosthesis comprising a cannulated tibial prosthetic stem component formed by a plurality of cannulated modular stem component pieces and tibial prosthetic instrumentalities and methods for installing the cannulated modular stem component pieces into a distal tibia and removing the cannulated modular stem component pieces from a distal tibia.

14 Claims, 16 Drawing Sheets

CANNULATED MODULAR TIBIAL STEM COMPONENT PIECES FOR USE IN TOTAL ANKLE ARTHROPLASTY AND SYSTEMS FOR INSTALLING AND REMOVING SAME

CROSS-REFERENCE TO RELATED APPLICATIONS

This application claims priority under 35 USC Section 119(e) to U.S. Provisional Patent Application No. 61/851,123, filed Mar. 4, 2013, the disclosure of which is incorporated herein by reference in its entirety.

This application also claims priority under 35 USC Section 119(e) to U.S. Provisional Patent Application No. 61/821,681 filed May 9, 2013, the disclosure of which is incorporated herein by reference in its entirety.

This application is a continuation-in-part patent application of U.S. patent application Ser. No. 13/573,887, filed Oct. 12, 2012, currently pending, and which is incorporated herein by reference in its entirety; and said U.S. patent application Ser. No. 13/573,887 is a continuation-in-part patent application of U.S. patent application Ser. No. 13/068,290, filed May 6, 2011, and issued Jul. 2, 2013 as U.S. Pat. No. 8,475,463, and which is incorporated herein by reference in its entirety; and said U.S. patent application Ser. No. 13/068,290 is a continuation-in-part patent application of U.S. patent application Ser. No. 12/798,417, filed Apr. 2, 2010, and issued Dec. 25, 2012 as U.S. Pat. No. 8,337,503, and which is incorporated herein by reference in its entirety; and said U.S. patent application Ser. No. 12/798,417 claims priority under 35 USC Section 119(e) to U.S. Provisional Patent Application No. 61/212,533, filed Apr. 13, 2009 and to U.S. Provisional Patent Application No. 61/270,203, filed Jul. 6, 2009, both disclosures of which are incorporated herein by reference in their entireties.

FIELD OF THE INVENTION

This invention relates generally to an ankle replacement prosthesis comprising a intramedullary or tibial prosthetic stem component formed by a plurality of modular stem component pieces and to instrumentalities and methods for installing the component pieces into and removing the component pieces from a distal tibia and, in particular, to an ankle replacement prosthesis comprising a cannulated intramedullary or tibial prosthetic stem component formed by a plurality of cannulated modular stem component pieces and to instrumentalities and methods for installing the cannulated modular stem component pieces into and removing the cannulated modular stem component pieces from a distal tibia.

BACKGROUND OF THE INVENTION

Total ankle replacement surgery, or total ankle arthroplasty, is an evolving area in orthopedic surgery. Recent advances in prosthetic devices and instruments for placement of the prostheses in the bone have made this a relatively common procedure. During the evolution of this procedure new problems are becoming apparent with existing systems, and there is a need to address some of these to improve the outcome of this type of surgery for patients.

One type of total ankle replacement has a tibial prosthetic component that has an intramedullary or tibial prosthetic stem component. This stem is constructed from smaller modular tibial stem component pieces that are assembled within the tibial-talar space. As each new piece is added to the existing stem, the entire construct is driven further into the intramedullary canal of the tibia. During the surgical procedure the surgeon will determine how many of the component pieces need to be combined to form the optimum construct for that patient.

A problem that needs to be addressed is the capability of removing an implanted tibial prosthetic stem component. Most commonly this would be required in the event of infection of the prosthesis. There is really no way to eradicate infection without removing the prosthesis. It is important to do this in a matter that is not destructive to the remaining bone for ensuring the possibility that a new prosthesis could be implanted after the infection had been adequately treated.

With existing techniques and instruments the prosthesis with an intramedullary or tibial prosthetic stem component is difficult to remove without significantly damaging the tibia bone. The outer surface of the tibial stem component pieces are covered with a material that the surrounding bone grows into. Separating the bone from the stem pieces without removing excessive bone, and thus making further surgical reconstruction impossible, is difficult.

For example, one existing technique for the removal of the tibial implant is the requirement for large bone windows to be cut into the lower end of the tibia to remove the stem component pieces of the tibial prosthetic stem component that have become fixed into the bone during the initial surgical procedures. The result of this bone destruction yields a tibia that makes further reconstructive procedures particularly problematic.

Accordingly, there is a particular need to overcome the significant shortcomings in the removal of the intramedullary or tibial prosthetic stem component pieces of the tibial implant from the distal tibia during revision surgical procedures.

BRIEF SUMMARY OF THE INVENTION

Applicants prior U.S. patent application Ser. No. 13/573,887, filed Oct. 12, 2012, which is incorporated herein by reference in its entirety, describes a system: methods and instrumentalities for removing an implanted tibial prosthetic stem component formed by a plurality of modular stem component pieces. That application describes a method and instrumentalities for drilling a channel in the talus and calcaneus bones that is aligned with the longitudinal axis of the implanted tibial prosthetic stem component. Through this channel a driving tool is passed. An offset chisel head or saw head that has been passed through an anterior wound at the front of the ankle is then engaged at the end of the driving tool in the tibial-talar space, and then the driving tool is manipulated to cut the bone away from the most inferior of the tibial stem component pieces. In one embodiment, a centering device that is screwed into the bore in the inferior surface of the tibial stem component piece helps to keep the chisel or saw aligned with the surface of the tibial stem component piece. Although superior to prior art methods, this may be a cumbersome system for surgeons to use.

Accordingly, and in one aspect, an embodiment of the invention provides a tibial prosthetic component comprised of a cannulated modular tibial prosthetic stem component formed from a plurality of cannulated modular tibial stem component pieces. The cannulated modular tibial stem component pieces are configured to combine or operatively couple together to form the cannulated modular tibial prosthetic stem component of the tibial prosthetic component. Each cannulated modular tibial stem component piece comprises an interior circumscribing surface defining an open ended bore longitudinally extending therethrough wherein the longitudinally extending open ended bore of each piece is aligned with its central long axis. Accordingly, when the cannulated modular tibial stem component pieces are operatively coupled together a central longitudinally extending stem bore or channel will traverse from a proximal end to a distal end of the cannulated modular tibial prosthetic stem component. In one embodiment, the central longitudinally extending stem bore or channel will have a diameter sufficient to allow passage of a central orthopedic alignment pin or guide wire along the longitudinal axis of the cannulated modular tibial prosthetic stem component.

In another aspect, an embodiment of the invention provides a cannulated driving tool that is passed through the aforementioned channel in the talus and calcaneus bones that is aligned with the longitudinal axis of the implanted cannulated modular tibial prosthetic stem component. In addition, an embodiment of the invention provides the aforementioned offset chisel head or saw head each having a central opening passing therethrough. The offset chisel head or saw head passes through an anterior wound at the front of the ankle and then engages the end of the cannulated driving tool in the tibial-talar space, and then the cannulated driving tool is manipulated to cut the bone away from the most inferior of the cannulated modular tibial stem component pieces utilizing the offset chisel or saw head.

During this process, it is an aspect of an embodiment of the invention to dispose the central alignment wire through the cannulated driving tool, the offset chisel or saw head, and each of the cannulated modular tibial stem component pieces of the implanted cannulated modular tibial prosthetic stem component to keep the offset chisel head or saw head aligned with the outer curvature of at least the inferior or lower most cannulated modular tibial stem component piece of the cannulated modular tibial prosthetic stem component. Accordingly, the central orthopedic alignment pin or wire that follows the central axis of the cannulated modular tibial prosthetic stem component centralizes the cutting head (e.g., the offset chisel head or saw head) utilizing the attached driving tool cannulated along its central axis. With the tibial prosthetic stem component cannulated, the central orthopedic alignment pin or guide wire passes through the cannulated modular tibial prosthetic stem component and through the cannulated driving tool comprising a cutting head (e.g., the offset chisel head or saw head) to maintain the cutting head aligned with the outer curvature of at least the inferior or lower most cannulated modular tibial stem component piece of the cannulated modular tibial prosthetic stem component to aid in accurate separation of the cannulated modular tibial prosthetic stem component from the surrounding bone.

Accordingly, it should be apparent that numerous modifications and adaptations may be resorted to without departing from the scope and fair meaning of the claims as set forth herein below following the detailed description of the invention.

DETAILED DESCRIPTION OF THE INVENTION

Figure 1:
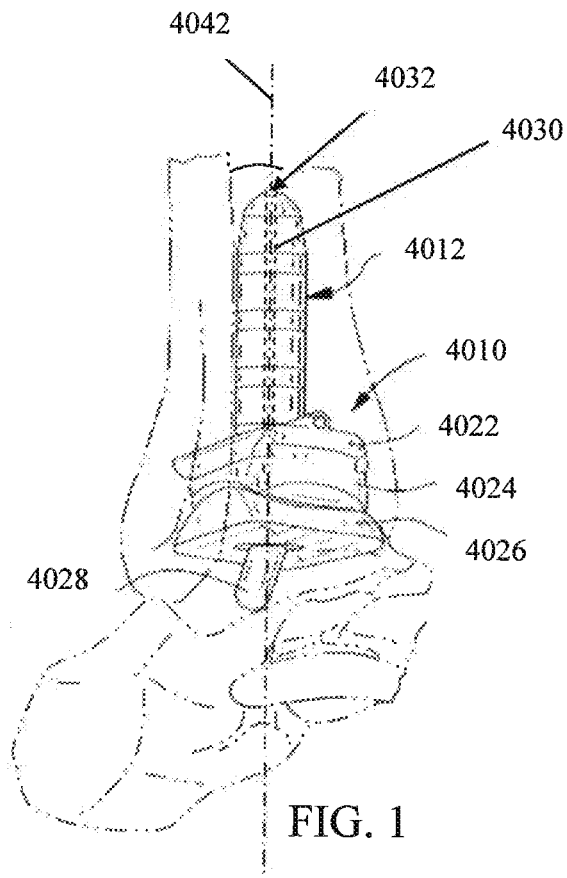
FIG. 1 is a side and front perspective view of a replacement of a total ankle joint with an embodiment of an ankle prosthesis comprised of a cannulated modular tibial prosthetic stem component or cannulated modular intramedullary stem component, a tibial tray component, a polyethylene spacer or poly insert component, a talar dome component, and a talar stem component.

In the drawings, like reference numerals denote like parts throughout the various drawing figures.

Systems and instrumentalities for use in total ankle replacement surgery are described in detail in Applicant's U.S. Pat. No. 8,337,503 and U.S. Pat. No. 8,475,463, which are both incorporated herein by reference in their entireties as though fully set forth herein.

Additionally, systems and instrumentalities for use in removal of tibial prostheses of total ankle replacements are described in detail in Applicant's U.S. Patent Application Publication No.: 2013/0046313, which is incorporated herein by reference in its entirety as though fully set forth herein.

Total Ankle Prosthesis 4010

In one embodiment, and referring to FIG. 1, prosthesis 4010 is comprised of a cannulated modular tibial prosthetic stem component 4012, a tibial tray component 4022, a polyethylene or poly insert component 4024, a talar dome component 4026, and a talar stem component 4028.

Additionally, the cannulated modular tibial prosthetic stem component 4012 comprises an open ended, interior circumscribing surface 4030 defining an open ended longitudinal stem channel or open ended central longitudinal bore 4032 passing through the cannulated modular tibial prosthetic stem component 4012 wherein the open ended central longitudinal bore 4032 comprises a central longitudinally extending stem axis 4042 substantially perpendicular to the superior and inferior ends of the cannulated modular tibial prosthetic stem component 4012.

Cannulated Modular Tibial Prosthetic Stem Component 4012

Figure 2:
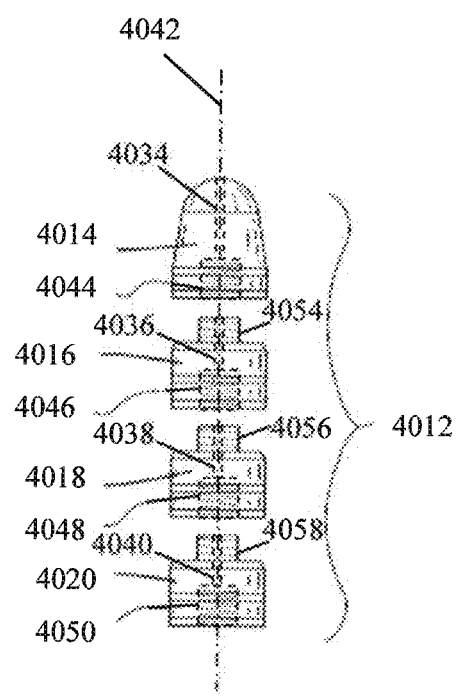
FIG. 2 is an exploded parts view of the cannulated modular tibial prosthetic stem component comprising a plurality of cannulated modular tibial stem component pieces.
Figure 3:
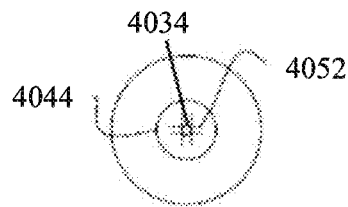
FIGS. 3 through 6 are bottom elevational views of the respective cannulated modular tibial stem component pieces illustrated in FIG. 2.
Figure 4:
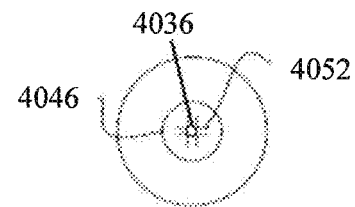
Figure 5:
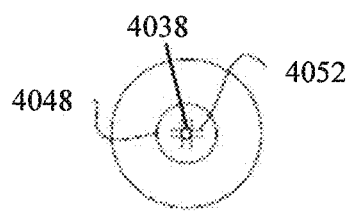
Figure 6:
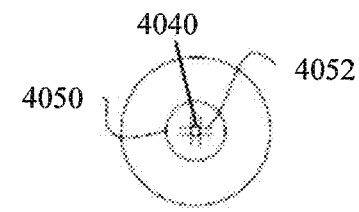

As illustrated in FIGS. 1 and 2, the cannulated modular tibial prosthetic stem component 4012 is comprised of a plurality of cannulated modular tibial prosthetic stem component pieces 4014, 4016, 4018, and 4020

The cannulated modular tibial stem component piece 4014 defines a superior stem component piece, the cannulated modular tibial stem component piece 4016 defines a first cannulated medial stem component piece, the cannulated modular tibial stem component piece 4018 defines a second cannulated medial stem component piece, and the cannulated modular tibial stem component piece 4020 defines a cannulated inferior stem component piece.

The cannulated modular tibial prosthetic stem component may range from 14-18 mm in diameter with a typical 4-piece construct measuring 50 mm in length. This is completely customizable per individual patient need. This segmented design allows for a less invasive approach in prosthetic placement, and more robust anchoring. The cannulated modular tibial stem component pieces 4014, 4016, 4018, and 4020 each have a specific height and diameter, and different sizes can be combined together to construct the final cannulated modular tibial prosthetic stem component 4012.

Additionally, and as illustrated in FIGS. 2 through 6, the cannulated modular tibial stem component pieces 4014, 4016, 4018, and 4020 respectively comprise threaded bores 4044, 4046, 4048, and 4050 extending through their posteriors ends and central channels or bores 4034, 4036, 4038, and 4040 extending through their superior ends so that each respective threaded bore and channel pair are in open communication with one another. Additionally, the cannulated modular tibial stem component piece 4020 comprises exteriorly threaded superior end 4058 that threadedly couples with the threaded bore 4048 of component piece 4018. Likewise, the cannulated modular tibial stem component piece 4018 comprises exteriorly threaded superior end 4056 that threadedly couples with the threaded bore 4046 of cannulated modular tibial stem component piece 4016 and, in turn, the cannulated modular tibial stem component piece 4016 comprises exteriorly threaded superior end 4054 that threadedly couples with the threaded bore 4044 of component piece 4014.

Accordingly, each threaded bore 4044, 4046, and 4048 has an internal diameter that is configured and sized to receive the outer diameter of each respective exteriorly threaded superior end or superior threaded protuberance 4054, 4056, and 4058 that extends out of a superior surface of each cannulated modular tibial stem component piece and includes external threads that are complemental to the internal threads in each threaded bore.

Hence, this allows the cannulated modular tibial stem component pieces 4014, 4016, 4018, and 4020 to be screwed together to form the final cannulated modular tibial prosthetic stem 4012 wherein the central channels or bores 4034, 4036, 4038, and 4040 of the respective cannulated modular tibial stem component pieces 4014, 4016, 4018, and 4020 form the open ended central longitudinal bore 4032 of the cannulated modular tibial prosthetic stem 4012.

FIGS. 3 through 6 also illustrate a recessed pattern 4052 disposed in a superior surface of each threaded bore 4044, 4046, 4048, and 4050. In one embodiment, the recessed pattern 4052 has a female cruciate slot pattern or shape.

Tibial Tray Component 4022

Figure 7:
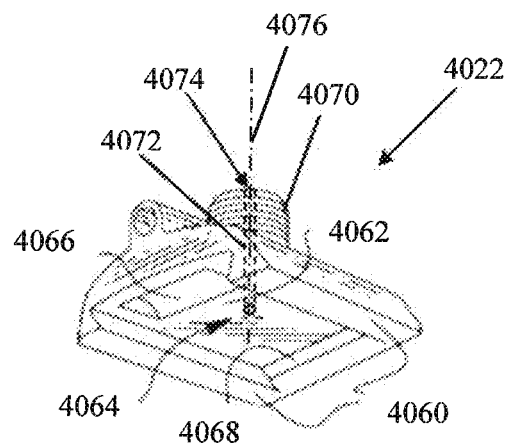
FIG. 7 is a side, front, and bottom perspective view of a cannulated tibial tray component having an open ended bore extending therethrough.

As illustrated in FIG. 7, the tibial tray component 4022 comprises oppositely spaced, inwardly tapered side rails 4060. The side rails 4060 extend in an anterior to posterior direction along the underside 4062 of the tibial tray component 4022. The tapered side rails 4060 form a channel 4064 between them. The underside 4062 of the tibial tray component 4022 includes a shaped depression or notch 4066 near its anterior edge and a stop flange 4068 near its posterior edge.

Additionally, the tibial tray component 4022 comprises a superior cannulated protuberance 4070 that extends out of a superior surface of the tibial tray component 4022 and that is sized to be received within bore 4050 of cannulated inferior stem component piece 4020 to couple thereto as illustrated in FIG. 1.

Furthermore, the superior cannulated protuberance 4070 comprises an open ended, interior circumscribing surface 4072 defining an open ended longitudinal protuberance channel or central protuberance bore 4074 passing through the cannulated protuberance 4070 wherein the open ended longitudinal protuberance channel 4074 comprises a central longitudinally extending protuberance axis 4076 substantially perpendicular to the superior end of the protuberance 4070 and to the underside 4062 of the tibial tray component 4022.

Figure 8:
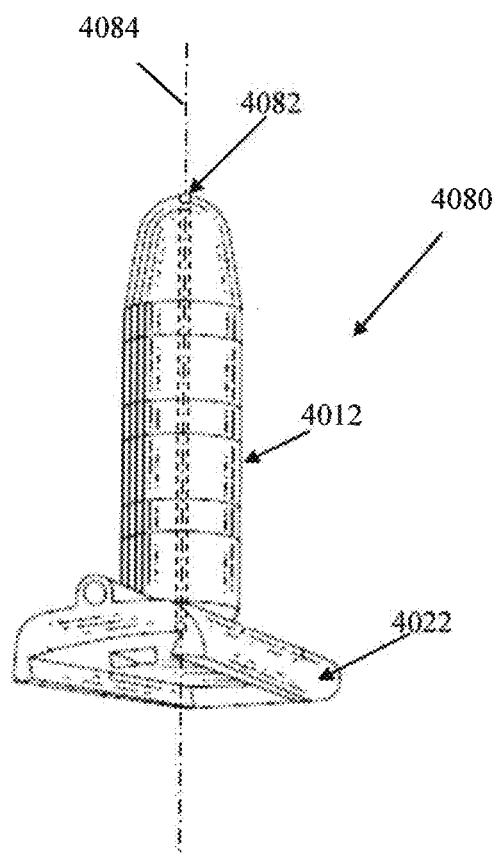
FIG. 8 is a side, front, and bottom perspective view of a cannulated tibial prosthetic component comprising the cannulated modular tibial prosthetic stem component and the cannulated tibial tray component.

Referring to FIG. 8, a tibial prosthetic component 4080 is defined by the cannulated modular tibial stem component pieces 4014, 4016, and 4018, being screwed together with the tibial stem component piece 4020 being fitted onto the superior cannulated protuberance 4070. In this configuration, the open ended central longitudinal bore 4032 will be collinear with the open ended longitudinal protuberance channel 4074 and the axis 4042 of the cannulated modular tibial prosthetic stem 4012 will align or be coincident with axis 4076 of the tibial tray component 4022 for defining an open ended longitudinal tibial prosthetic component channel or bore 4082 having a central longitudinally extending tibial prosthetic component axis 4084 of the tibial prosthetic component 4080. Accordingly, the open ended longitudinal tibial prosthetic component channel or bore 4082 extends from the most proximal portion of the tibial stem piece 4014 to the distal portion or the underside 4062 of the tibial tray component 4022.

In one embodiment, the common diameter of each of the bores 4044, 4046, and 4048, and 450 of the respective cannulated modular tibial stem component pieces 4014, 4016, 4018, and 4020 is between about 1 mm and about 6 mm.

Orthopedic Pin or Guide Wire 4090

Figure 9:
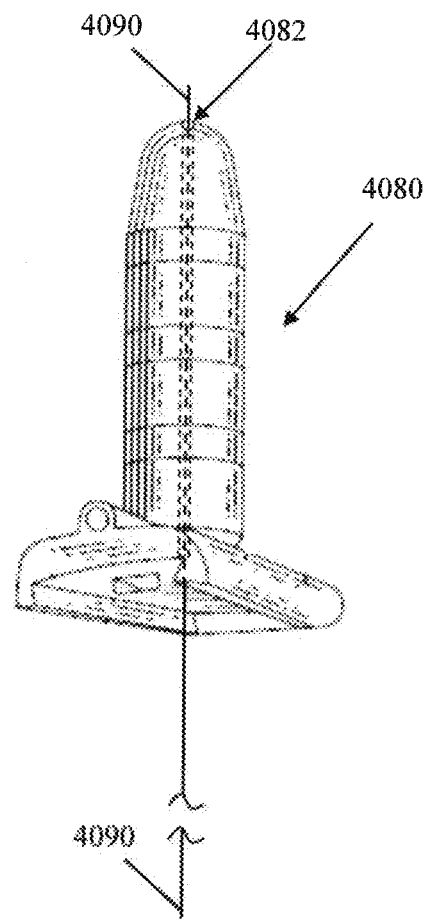
FIG. 9 is a side, front, and bottom perspective view of the cannulated modular tibial prosthetic stem component and a central orthopedic alignment pin or guide wire extending through a longitudinal bore disposed in the cannulated tibial tray component and in each respective cannulated modular tibial stem component piece of the cannulated modular tibial prosthetic stem component.

As illustrated in FIG. 9, an elongated orthopedic alignment pin or guide wire 4090 is provided and sized to pass through the open ended longitudinal tibial prosthetic component channel or bore 4082 of the tibial prosthetic component 4080. Accordingly, the orthopedic pin or guide wire 4090 is provided and sized to pass through the open ended central longitudinal bore 4032 of the cannulated modular tibial prosthetic stem 4012 and the open ended longitudinal protuberance channel 4074 of the tibial tray component 4022.

Figure 10:
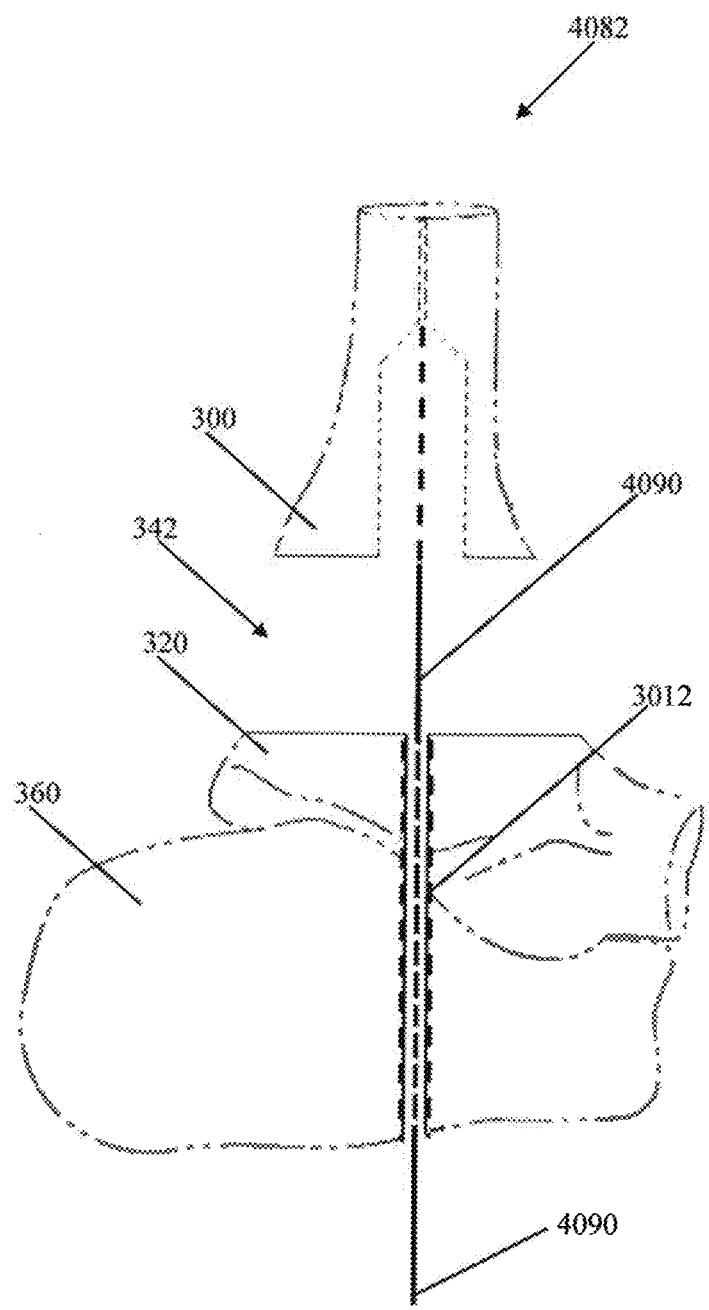
FIG. 10 is a fragmented view of the calcaneus and talus having a channel disposed therethrough wherein the channel has a central long axis coextensive or coincident with a bore in the tibia and further illustrating a side elevational view of the central orthopedic alignment pin or guide wire passing through the channel in the calcaneus and talus and into the bore in the tibia.

Referring to FIG. 10, the orthopedic pin or guide wire 4090 is sized and configured to pass through a channel 3012 formed in the calcaneus 360 and talus 320 and up through the tibial-talar space 342.

Figure 11:
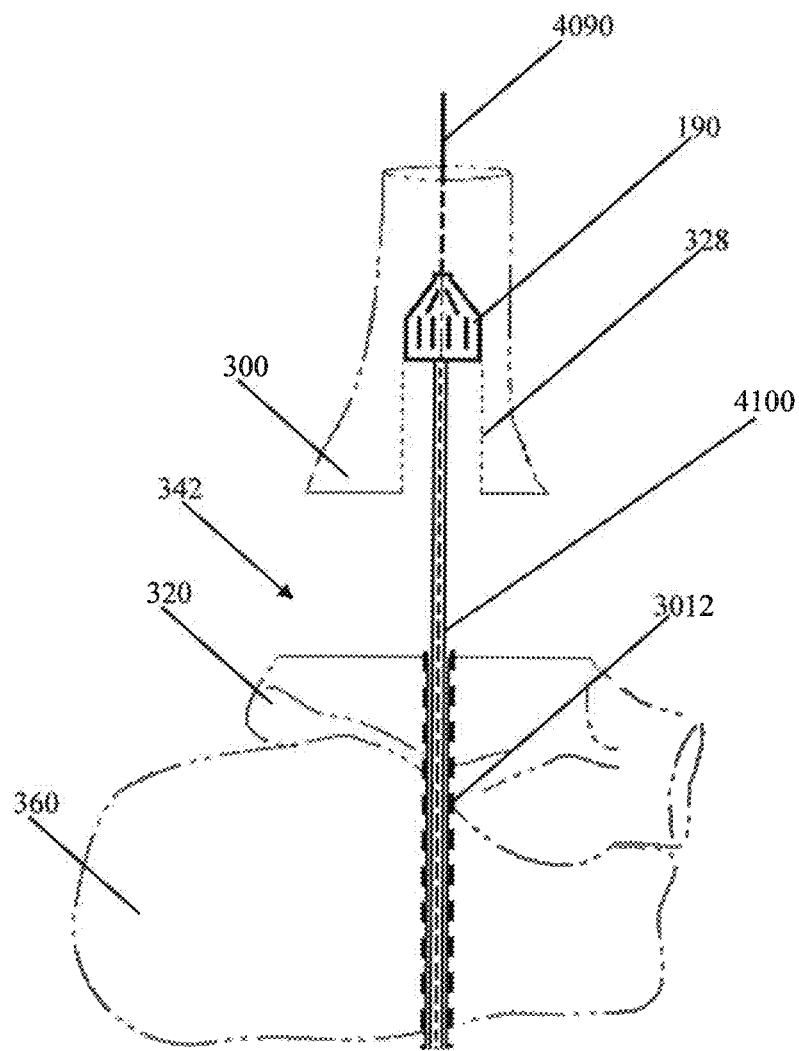
FIG. 11 is a side elevational view of the central orthopedic alignment pin or guide wire passing through channel in the calcaneus and talus and into the bore in the tibia and passing through a cannulated screwdriver surmounted by a cannulated reaming bit that is used to bore the bore in the distal tibia.

In use and operation, and referring to FIG. 11, the elongated orthopedic pin or guide wire 4090 may be utilized to align a cannulated reaming bit 190 driveably engaged with and surmounting a cannulated screwdriver 4100 which are utilized to bore a bore 328 into the distal tibia as illustrated.

Figure 12:
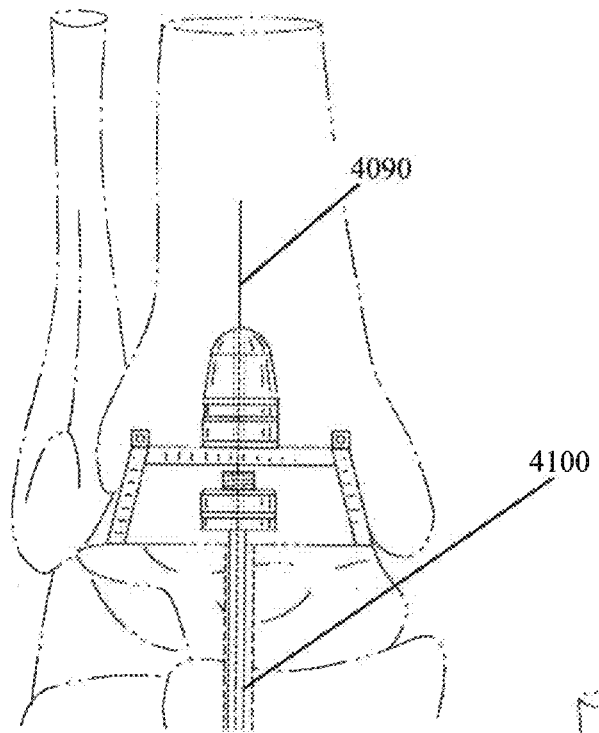
FIG. 12 is a front elevational view of the central orthopedic alignment pin or guide wire passing through channel in the calcaneus and talus and into the bore in the tibia and passing through a cannulated modular tibial stem component piece surmounting the cannulated screwdriver and through one or more cannulated modular tibial stem component pieces disposed within the bore in the distal tibia.
Figure 13:
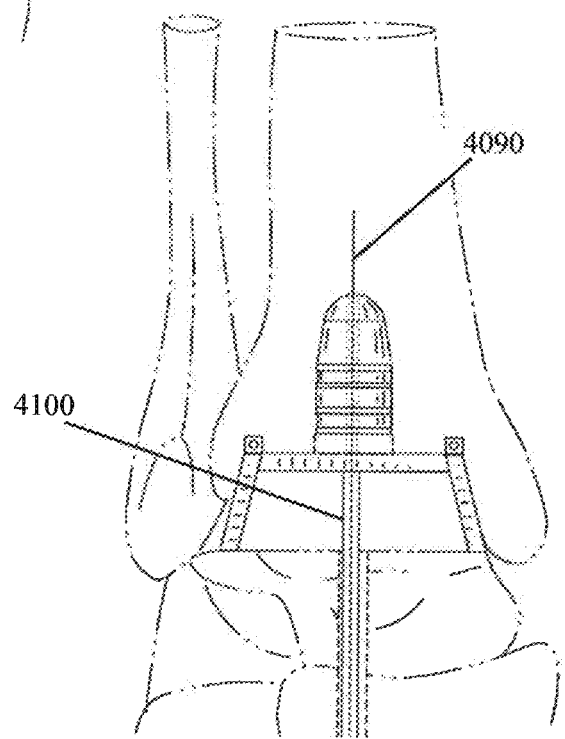
FIG. 13 is a front elevational view of the central orthopedic alignment pin or guide wire passing through channel in the calcaneus and talus, through the cannulated screwdriver, and through the inferior most cannulated modular tibial stem component screwed into the penultimate cannulated modular tibial stem component piece disposed within the bore in the distal tibia.

Referring to FIGS. 12 and 13, the elongated orthopedic pin or guide wire 4090 may be utilized to sequentially place the cannulated modular tibial stem component pieces 4014, 4016, 4018, and 4020 into the tibial bore with a cannulated screwdriver 4100 being passed over orthopedic pin or guide wire 4090 and through channel 3012 to sequentially screw cannulated modular tibial stem component piece 4016 to 4014, 4018 to 4016, and 4020 to 4018 by, for example, having the screwdriver head patterned complemental to recessed pattern 4052 in the respective cannulated modular tibial stem component pieces 4016, 4018, and 4020.

Moreover, the elongated orthopedic pin or guide wire 4090 may be utilized to align an offset chisel head 4432 or a cylindrical saw head 4454 along the longitudinal axis 4042 of the cannulated modular tibial prosthetic stem component 4012 when the offset chisel head 4432 or cylindrical saw head 4454 are used to cut the tibia bone 300 away from the cannulated modular tibial stem component pieces 4014, 4016, 4018, and 4020.

Circumferentially Cutting Tibia Circumscribing Inferior Most Stem Piece

Offset Chisel Device 4110

Figure 14:
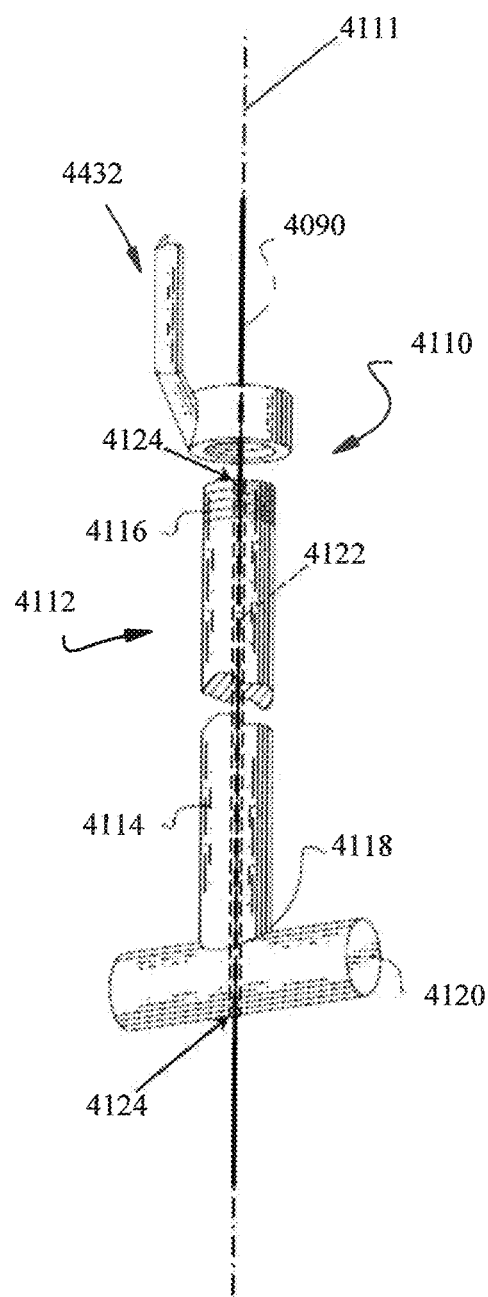
FIG. 14 is an exploded parts view of an embodiment of a bone cutting means in the form of an embodiment of a cannulated offset chisel device comprised of a cannulated offset chisel head surmounting one end of a cannulated driving tool having an open ended bore extending longitudinally therethrough wherein the cannulated driving tool is defined by a cannulated shaft having a cannulated handle disposed at an opposing end thereof and further illustrating the central orthopedic alignment pin or guide wire passing through the bore of the cannulated driving tool and the cannulated offset chisel device.

Referring now to FIG. 14, an embodiment of the bone cutting means is in the form of but not limited to, a cannulated offset chisel device 4110 having a central longitudinal axis 4111. The offset chisel device 4110 is comprised of a cannulated driving tool 4112 and an offset chisel head 4432. The cannulated driving tool 4112 comprises an elongated cannulated shaft 4114 sized and configured to pass through the channel 3012 (FIG. 10) formed in the calcaneus 360 and talus 330 and up through the tibial-talar space 342.

In one embodiment, the elongated cannulated shaft 4114 is cylindrically shaped with a diameter that slideably fits within channel 3012.

Additionally, the cannulated shaft 4114 comprises a threaded proximal end 4116 that is sized to pass through channel 3012 and an opposing distal end 4118 that, in one embodiment, terminates to a handle 4120 for grasping.

Furthermore, the cannulated shaft 4114 comprises a centrally disposed and a longitudinally extending interior circumscribing surface 4122 defining an open ended longitudinal bore 4124 having a longitudinal axis coincident with central longitudinal axis 4111 of the cannulated offset chisel device 4110. The longitudinal bore 4124 is configured with a diameter to allow passage of the elongated orthopedic pin or guide wire 4090 therethrough.

Figure 15:
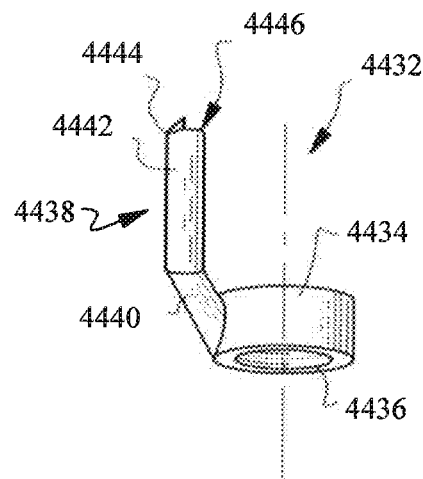
FIG. 15 is a side elevational view of the cannulated offset chisel head illustrated in FIG. 14.

FIG. 15 illustrates the offset chisel head 4432 of the cannulated offset chisel device 4110. The offset chisel head 4432 is comprised of a hollow annular base 4434 having a central threaded interior surface 4436 defining a central cannula shaped opening for the threaded proximal end 4116 of the cannulated shaft 4114 to pass into and threadedly couple therewith such that the central longitudinal axis of the shaft is coincident with the central longitudinal axis of the hollow annular base 4434.

Figure 16:
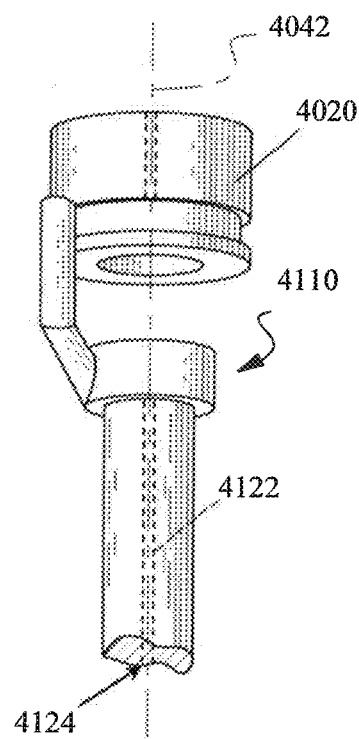
FIG. 16 is a side elevational view of an embodiment of a cannulated modular tibial stem component piece, a side elevational view of the cannulated offset chisel head having a chisel with a radius of curvature matching or complemental to a radius of an exterior curvature of the cannulated modular tibial stem component piece, and a fragmented view of the cannulated shaft of the cannulated driving tool operatively coupled to the cannulated offset chisel head.

Offset from the opening of the hollow annular base 4434 is an offset chisel 4438. The chisel 4438 includes an offset portion 4440 upwardly and outwardly diverging from the exterior surface of the hollow annular base 4434 and a cutting portion or blade 4442 upwardly transitioning away from the offset portion 4440 in a direction that is parallel with the central longitudinal axis of the offset chisel device 4110 or, in other words, the central longitudinal axis of the hollow annular base 4434 and cannulated shaft 4114. The cutting portion or blade 4442 of the offset chisel head 4432 is formed with at least a superior sharp edge 4444 and has a radius of curvature 4446 that matches the radius of curvature of the most inferior tibial stem component piece as illustrated in FIG. 16.

Figure 17:
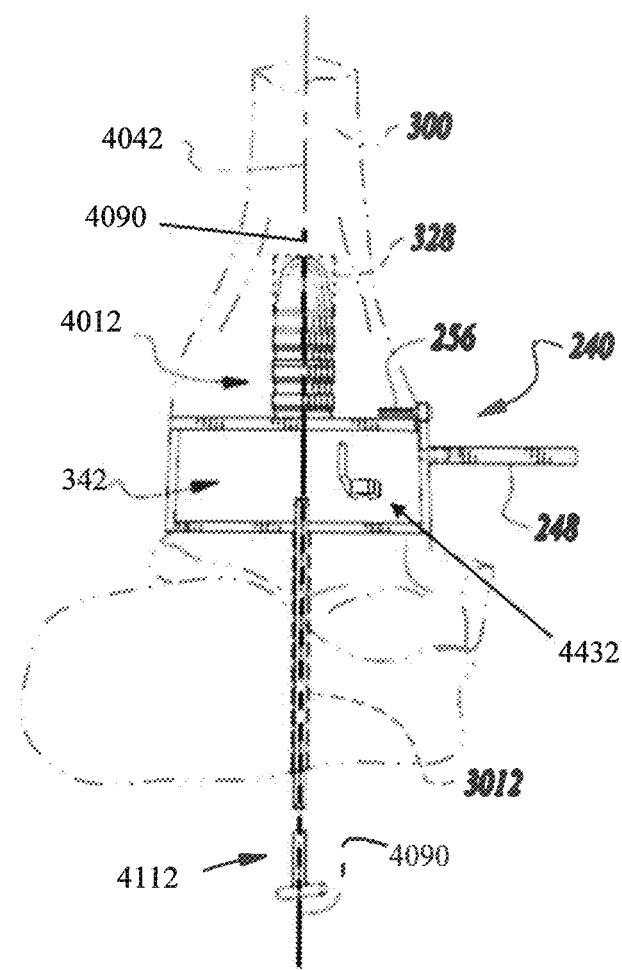
FIG. 17 is a side elevational view of a skeleton cage or frame positioned in the tibial-talar space, a side elevational view of the cannulated modular tibial prosthetic stem component, and a side elevational view of the cannulated offset chisel head, and a side elevational view of the cannulated shaft of the cannulated driving tool passing through the channel in the calcaneus and talus, and a side elevational view of the central orthopedic alignment pin or guide wire passing through the cannulated driving tool and the cannulated modular tibial prosthetic stem component.

As illustrated in FIG. 17, the cannulated shaft 4114 of the cannulated driving tool 4112 is configured with an outside diameter small enough to allow passage of the cannulated shaft 4114 through the channel in the calcaneus and talus and into the tibial-talar space while allowing the central orthopedic alignment pin or guide wire 4090 to pass through the bore 4124 of the cannulated shaft 4114.

Figure 18:
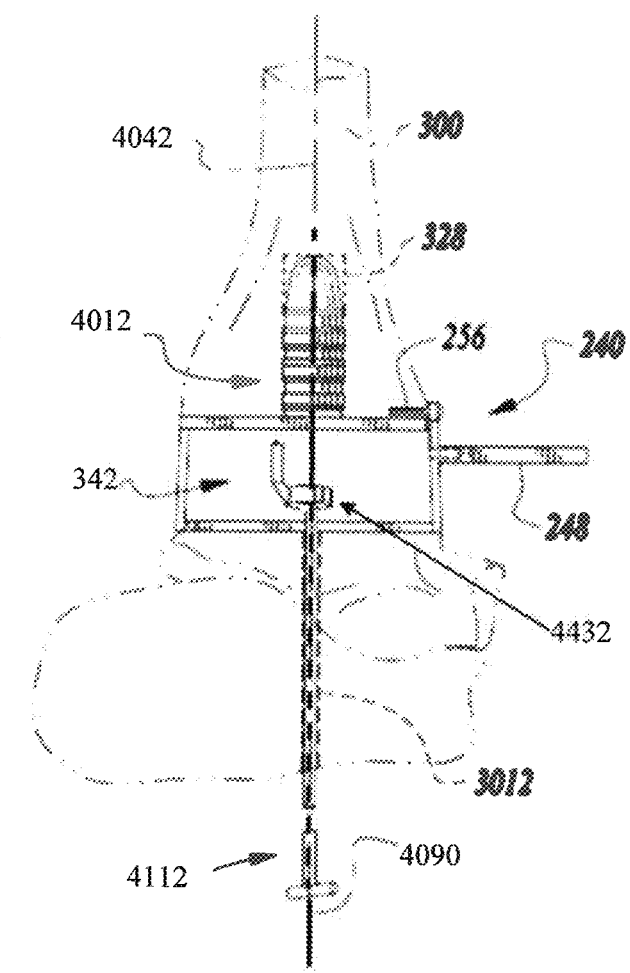
FIG. 18 is a side elevational view of a skeleton cage or frame positioned in the tibial-talar space, a side elevational view of the cannulated modular tibial prosthetic stem component, and a side elevational view of the cannulated offset chisel head surmounting the cannulated shaft of the cannulated driving tool passing through the channel in the calcaneus and talus, and a side elevational view of the central orthopedic alignment pin or guide wire passing through the cannulated driving tool, the cannulated offset chisel head, and the cannulated modular tibial prosthetic stem component.

In FIG. 18, the cannulated driving tool 4112 is illustrated being passed through the channel in the calcaneus and talus and into the tibial-talar space with the offset chisel head 4432 surmounting the cannulated driving tool 4112 in the tibial-talar space 342 while allowing the central orthopedic alignment pin or guide wire 4090 to pass through the bore 4124 of the cannulated shaft 4114 and into the open ended central longitudinal bore 4032 of the cannulated modular tibial prosthetic stem component 4012. In this manner, the orthopedic alignment pin or guide wire 4090 aligns the offset chisel head 4432 with the outer curvature of at least the inferior or lower most cannulated modular tibial stem component piece of the cannulated modular tibial prosthetic stem component 4012 to aid in accurate separation of the cannulated modular tibial prosthetic stem component 4012 from the surrounding bone.

In one configuration, the offset chisel 4438 should be of a length that allows it to just pass beyond vertical surface of the body of the most inferior tibial stem component piece.

Accordingly, the offset chisel device 4110 that is used at any given time may be sized in accordance with the size of the most inferior tibial stem component piece that is currently being removed.

As illustrated in FIGS. 17 and 18, the offset chisel device 4110 is designed to be assembled by passing the cannulated shaft 4114 through the channel 3012 and then have the offset chisel head 4432 placed into the tibial-talar space 342 from the anterior incision and central anterior open portion of a skeleton cage or frame 240 positioned within the tibial-talar space 342 via handle 248. The threaded proximal end 4116 of the cannulated shaft 4114 then engages the central threaded interior surface 4436 of the hollow annular base 4434 of the offset chisel head 4432.

With the orthopedic alignment pin or guide wire 4090 in place as illustrated in FIGS. 17 and 18, the offset chisel device 4110 is then reciprocated to free any bone around the sides of the inferior most cannulated stem piece of the in situ cannulated modular tibial prosthetic stem component 4012 that is to be removed.

Preferably, the height of the offset chisel 4438 is approximately the height of the inferior most cannulated stem piece of the in situ cannulated modular tibial prosthetic stem component 4012. It cannot be substantially larger, because it must be small enough to fit into the tibial-talar space 342.

In one embodiment, each offset chisel device 4110 is made out of, but not limited to, a metal material.

Cylindrical Saw Device 4450

Figure 19:
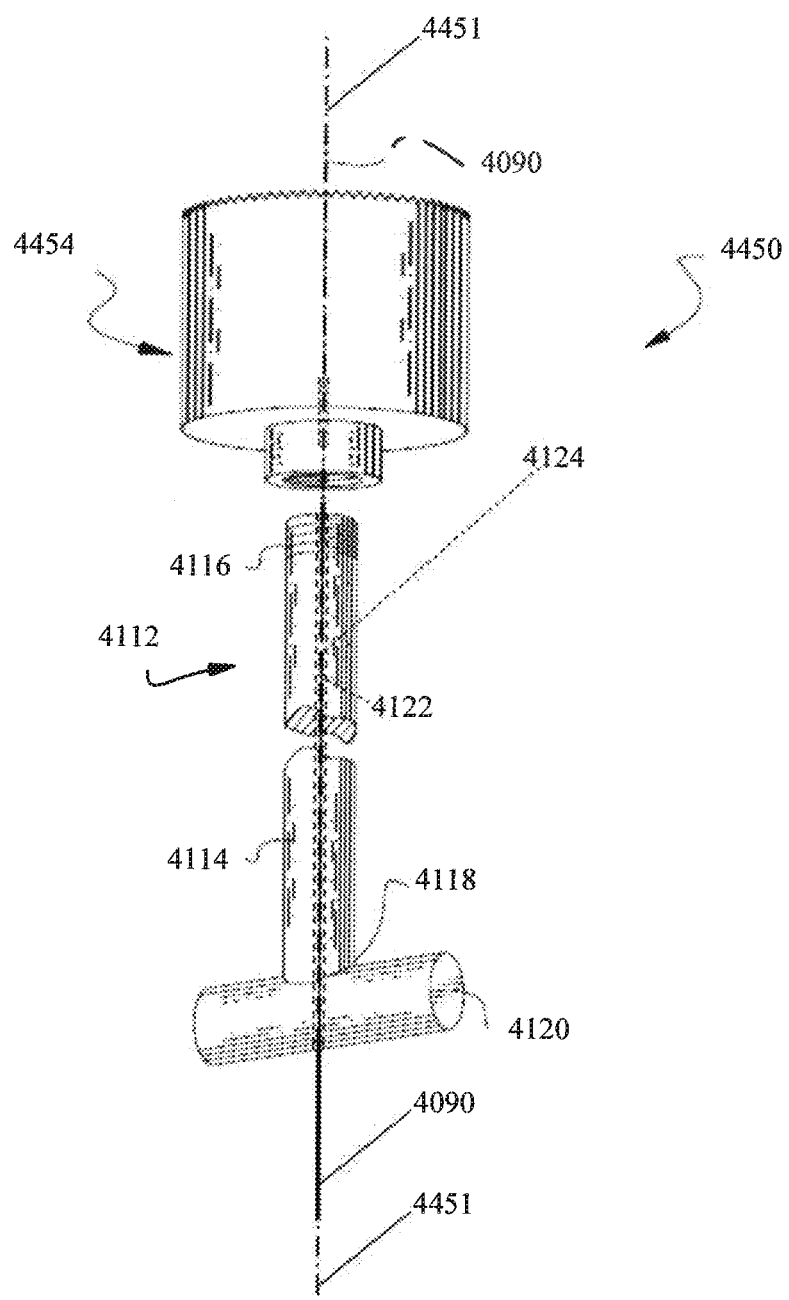
FIG. 19 is an exploded parts view of an embodiment of a bone cutting means in the form of an embodiment of a cannulated saw device comprised of a cannulated cylindrical saw head surmounting one end of the cannulated driving tool and further illustrating the central orthopedic alignment pin or guide wire passing through the bore of the cannulated driving tool and the saw head.

Referring now to FIG. 19, and in another embodiment, the bone cutting means is in the form of, but not limited to, a cannulated saw device 4450 having a central longitudinal axis 4451. The cannulated saw device 4450 comprises a cannulated cylindrical saw head 4454 detachably coupled to the cannulated driving tool 4112 delineated in detail above. Similar to the offset chisel device 4110, the central orthopedic alignment pin or guide wire 4080 passes through the bore of the cannulated driving tool 4112 and the cannulated cylindrical saw head 4454.

Cannulated Cylindrical Saw Head 4454

Figure 20:
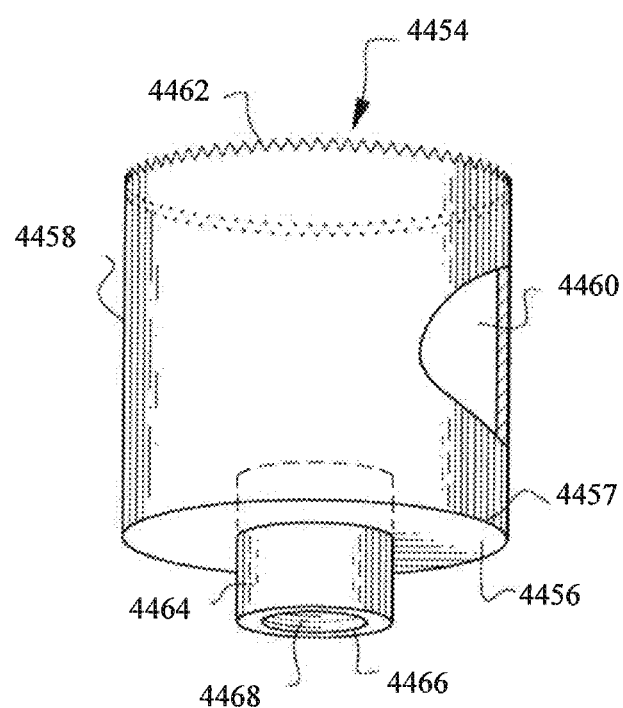
FIG. 20 is a side elevational and partial cutaway view of the saw head illustrated in FIG. 19.

Referring to FIG. 20, the cannulated cylindrical saw head 4454 comprises an inferior circular base 4456 having an outer circumscribing periphery 4457 transitioning into a cylindrically shaped side wall 4458 arising from the inferior circular base 4456 forming a shell of a cylinder and defining an internal cylindrically shaped cavity 4460. The cylindrically shaped side wall 4458 terminates to superior circular cutting edge or cutting rim 4462.

There are different sizes of the cylindrical saw head 4454 corresponding to different sizes of the cannulated modular tibial stem component pieces 4014, 4016, 4018, and 4020 forming different sizes of cannulated modular tibial prosthetic stem component 4012. The chosen saw diameter and depth should allow the most inferior cumulated modular tibial stem component piece that is being removed to fit within the cavity 4460 of the cylindrical saw head 4454. Thus, for each cannulated modular tibial stem component piece the internal diameter of the cylindrical saw head 4454 or the diameter of cavity 4460, should be just greater than the diameter of the most inferior cannulated modular tibial stem component piece being removed, and the internal depth of the cylindrical saw head 4454 or cavity 4460 minus the height of an interior portion of an interior protruding member 4464 should be just greater than the height of the most inferior cannulated modular tibial stem component piece being removed.

Preferably, the cylindrical saw had 4454 has a very thin cylindrically shaped side wall for ensuring that the kerf of the circumscribing bone cut from the sides of the most inferior cannulated modular tibial stem component piece is minimal during the removal thereof.

The cylindrical saw head 4454 further comprises the cylindrically shaped protruding member 4464 extending superiorly and inferiorly from the surfaces of the circular base 4456. The protruding member 4464 comprises a circular opening 4466 extending therethrough and defined by a central threaded interior surface 4468 having threads complemental to the threaded proximal end 4116 of the cannulated driving tool 4112 for threadedly coupling thereto.

In one embodiment, the cylindrical saw head 4454 is made out of, but not limited to, a metal material.

Figure 21:
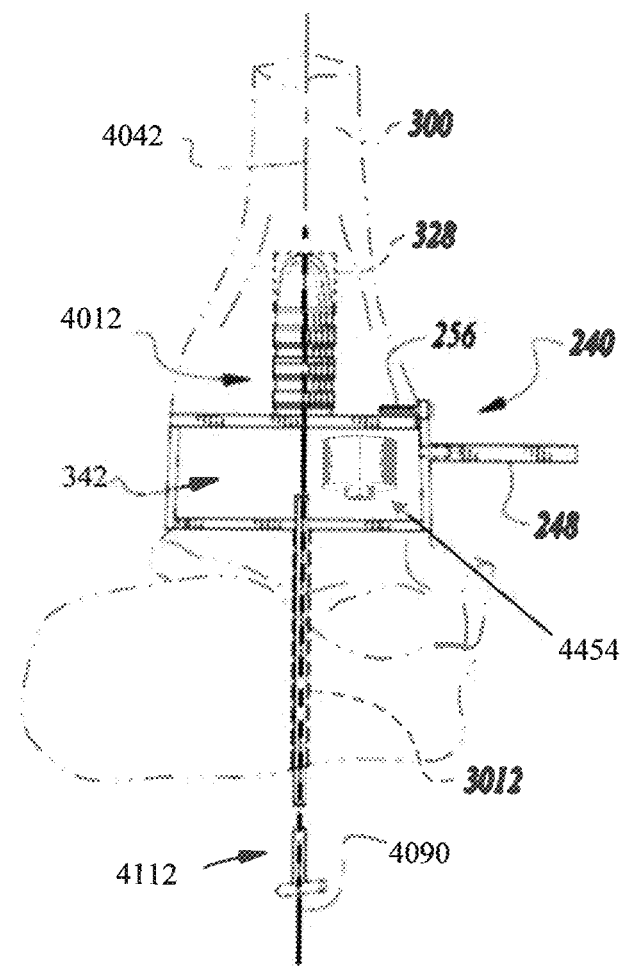
FIG. 21 is a side elevational view of the skeleton cage or frame positioned in the tibial-talar space, a side elevational view of the cannulated modular tibial prosthetic stem component, and a side elevational view of the saw head, and a side elevational view of the cannulated shaft of the cannulated driving tool passing through the channel in the calcaneus and talus, and a side elevational view of the central orthopedic alignment pin or guide wire passing through the cannulated driving tool and the cannulated modular tibial prosthetic stem component.
Figure 22:
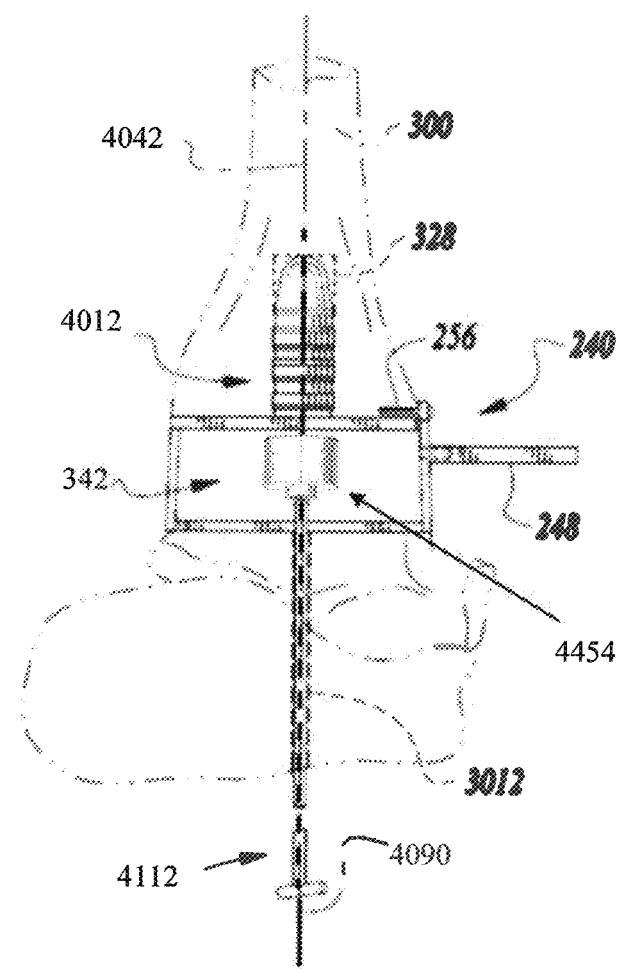
FIG. 22 is a side elevational view of a skeleton cage or frame positioned in the tibial-talar space, a side elevational view of the cannulated modular tibial prosthetic stem component, and a side elevational view of the saw head surmounting the cannulated shaft of the cannulated driving tool passing through the channel in the calcaneus and talus, and a side elevational view of the central orthopedic alignment pin or guide wire passing through the cannulated driving tool, saw head, and the cannulated modular tibial prosthetic stem component.

Referring now to FIGS. 21 and 22, and similar to FIGS. 17 and 18, the cylindrical saw device 4450 is designed to be assembled by passing the cannulated shaft 4114 of the cannulated driving tool 4112 through the channel 3012 and into the tibial-talar space 342 and then have the cylindrical saw head 4454 placed into this space from the anterior incision and central anterior open portion of the skeleton cage or frame 240 held in place with at least one screw 256. The threaded proximal end 4116 of the cannulated shaft 4114 then engages the central threaded interior surface 4468 of the protruding member 4464 of the cylindrical saw head 4454.

As delineated, above, the cannulated shaft 4114 of the cannulated driving tool 4112 is configured to allow the passage of the central orthopedic alignment pin or guide wire 4090 therethrough and into the open ended central longitudinal bore 4032 of the cannulated modular tibial prosthetic stem component 4012. In this manner, the orthopedic alignment pin or guide wire 4090 aligns the cylindrical saw head 4454 over the inferior or lower most cannulated modular tibial stem component piece of the cannulated modular tibial prosthetic stem component 4012 being removed.

Then, the cannulated saw device 4450 is rotated for cutting a circumscribing cut around and adjacent to the exterior circumscribing side surface of the inferior or lower most cannulated modular tibial stem component piece of the in situ tibial cannulated modular tibial prosthetic stem component 4012 that is to be removed.

In another embodiment, the cannulated driving tool 4112 is devoid of the handle 4120 adjacent distal end 4118 such that the distal end 4118 can be operatively coupled to and driven by, for example, a drill for rotating cylindrical saw head 4454 for cutting a circumscribing cut around and adjacent to the exterior circumscribing side surface of the inferior or lower most cannulated modular tibial stem component piece of the in situ tibial cannulated modular tibial prosthetic stem component 4012 that is to be removed.

In Use and Operation

In use and operation, and referring to the drawings, an embodiment of a tibial prosthesis removal system: methods and instrumentalities is illustrated for removing an embodiment of a tibial prosthetic component 4080 having an cannulated modular tibial prosthetic stem component 4012 comprised of a plurality of cannulated modular tibial stem component pieces 4014, 4016, 4018, and 4020 disposed in a tibial blind bore 328. Following an anterior ankle skin incision, the polyethylene insert component 4024, the talar dome component 4026, and the talar stem component 4028 are removed from the in situ total ankle prosthesis 4010 while the tibial prosthetic component 4080 comprised of a plurality of cannulated modular tibial stem component pieces and the tibial tray component 4022 remain in situ.

With these components removed, a channel 3012 is formed through the talus 330 and the calcaneus 360 that is substantially axially aligned with the longitudinal axis 4042 of the in situ cannulated modular tibial prosthetic stem component 4012 even if the cannulated modular tibial prosthetic stem component 4012 has shifted into a slight angulation off the alignment of the original insertion axis by the process delineated in Applicant's U.S. Pat. No. 8,337,503 and U.S. Pat. No. 8,475,463, which are both incorporated herein by reference in their entireties as though fully set forth herein. Or, the process delineated in Applicant's U.S. Patent Application Publication No.: 20130046313 which is incorporated herein by reference in its entirety as though fully set forth herein.

The forming of channel 3012 allows a series of instrumentalities, as delineated above, to pass through the channel 3012 to aid in removing the plurality of cannulated modular tibial stem component pieces of the cannulated modular tibial prosthetic stem component 4012 as delineated above.

In review, the bone cutting means as delineated hereinabove are utilized for cutting the tibial bone attached to the walls of the most inferior cannulated modular tibial stem component piece until the bone has been cut completely away from the most inferior cannulated modular tibial stem component piece circumferentially. Then, the bone cutting means is removed. Next, the cannulated screwdriver 4100 is utilized as delineated above to remove the most inferior cannulated modular tibial stem component piece. This process is repeated until all of the cannulated modular tibial stem component pieces of the cannulated modular tibial prosthetic stem component 4012 have been removed.

Central Insert Pin

Figure 23:
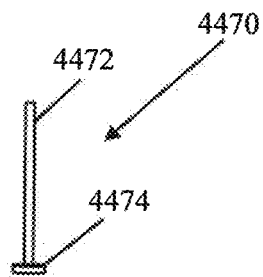
FIG. 23 is a side elevational view of a central insert pin.

In one embodiment, and referring to FIG. 23, prosthesis 4010 is further comprised of a central insert pin 4470 having an elongated shaft 4472 with an inferior end attached to a disk shaped head 4474

Figure 24:
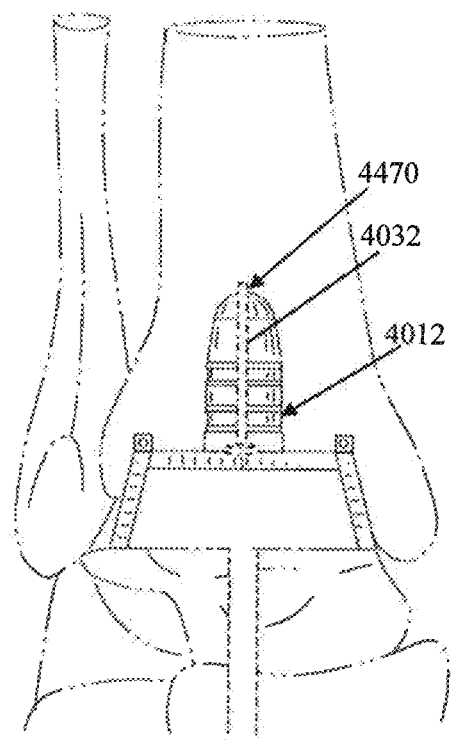
FIG. 24 is a front elevational view of the central insert pin disposed in the cannulated modular tibial stem component piece disposed within the bore in the distal tibia.

In use and operation, referring to FIG. 24, central insert pin 4470 passes through the open ended central longitudinal bore 4032 passing through the cannulated modular tibial prosthetic stem component 4012 so that no bone grows into the bore 4032. Then, when the cannulated modular tibial prosthetic stem component 4012 needs to be removed in the future, the insert can be withdrawn, and the canal or bore 4032 will be free for insertion of the wire 4090 as delineated above. The elongated shaft 4472 may have a diameter of 1-6 mm, and the cannulated canals bore 4032 in the stem pieces may also have a diameter of 1-6 mm.

The above detailed description demonstrates the industrial applicability of this invention.

Moreover, it should be apparent that numerous modifications and adaptations may be resorted to without departing from the scope and fair meaning of the instant invention as set forth hereinabove and as described herein below by the claims.

I claim:

1. A tibial prosthetic component comprising:
a plurality of modular tibial stem component pieces configured to detachably couple together to form a modular tibial prosthetic stem component having a longitudinal axis;
an interior circumscribing surface centrally disposed and axially extending through said modular tibial prosthetic stem component, said interior circumscribing surface defining a central longitudinal open ended bore extending along said longitudinal axis of said modular tibial prosthetic stem component for defining a cannulated modular tibial prosthetic stem component; and
wherein each of said plurality of modular tibial stem component pieces comprises a centrally disposed and axially extending interior circumscribing component piece surface forming a distinct portion of said interior circumscribing surface of said cannulated modular tibial prosthetic stem component.

2. The tibial prosthetic component of claim 1 further comprising a tibial tray component comprising a centrally disposed and axially extending interior circumscribing surface defining an open ended tibial tray component bore and wherein said tibial tray component is configured to detachably couple to an inferior most end of said cannulated modular tibial prosthetic stem component with said open ended tibial tray component bore extending along said longitudinal axis of said cannulated modular tibial prosthetic stem component.

3. The tibial prosthetic component of claim 1 wherein said central longitudinal open ended bore of said cannulated modular tibial prosthetic stem component is configured with a diameter to allow passage of a central alignment wire through said cannulated modular tibial prosthetic stem component along said longitudinal axis of said cannulated modular tibial prosthetic stem component.

4. The tibial prosthetic component of claim 3 wherein said diameter of said central longitudinal open ended bore of said cannulated modular tibial prosthetic stem component is between about 1.0 millimeters to about 6.0 millimeters.

5. A tibial prosthetic component comprising:
a plurality of cannulated modular tibial stem component pieces each comprising a centrally disposed and axially extending interior circumscribing surface defining an open ended longitudinal bore; and means for detachably coupling said plurality of cannulated modular tibial stem component pieces together to form a cannulated modular tibial prosthetic stem component having a central longitudinally extending open ended bore having a distinct portion formed by each interior circumscribing surface of said plurality of cumulated modular tibial stem component pieces.

6. The tibial prosthetic component of claim 5 further comprising a tibial tray component comprising a centrally disposed and axially extending interior circumscribing surface defining an open ended tibial tray component bore and wherein said tibial tray component is configured to detachably couple to an inferior most end of said cannulated modular tibial prosthetic stem component with said open ended tibial tray component bore extending along a central longitudinal axis of said cannulated modular tibial prosthetic stem component.

7. The tibial prosthetic component of claim 5 wherein said central longitudinally extending open ended bore of said cannulated modular tibial prosthetic stem component is configured with a diameter to allow passage of a central alignment wire through said cannulated modular tibial prosthetic stem component along a central longitudinal axis of said cannulated modular tibial prosthetic stem component.

8. The tibial prosthetic component of claim 7 wherein said diameter of said central longitudinally extending open ended bore of said cannulated modular tibial prosthetic stem component is between about 1.0 millimeters to about 6.0 millimeters.

9. A tibial prosthetic removal system for removing a cannulated modular tibial prosthetic stem component disposed within a distal tibia; said tibial prosthetic removal system comprising:

a cannulated drive shaft comprising an open ended, interior circumscribing surface defining an open ended central shaft bore passing through said cannulated drive shaft and having a central longitudinally extending shaft bore axis;

said cannulated drive shaft configured to pass through a channel formed in a calcaneus and talus and up through a tibial-talar space disposed adjacent the distal tibia having the cannulated modular tibial prosthetic stem component disposed therein, the cannulated modular tibial prosthetic stem component formed from a plurality of detachably coupled together cannulated modular tibial stem component pieces each comprising a centrally disposed and axially extending interior circumscribing surface defining an open ended longitudinal bore that together define a central open ended longitudinal stem bore of the cannulated modular tibial prosthetic stem component having a central longitudinally extending stem axis; and a guide wire configured to be received through said open ended central shaft bore of said cannulated drive shaft and through the central open ended longitudinal stem bore of the cannulated modular tibial prosthetic stem component disposed within the distal tibia to align in a substantially coincident location said central longitudinally extending shaft bore axis with the central longitudinally extending stem axis of the cannulated modular tibial prosthetic stem component.

10. The system of claim 9 further comprising an offset chisel head configured to be disposed within the tibial-talar space and surmounting one end of said cannulated drive shaft for circumferentially cutting bone around at least an inferior most cannulated modular tibial stem component piece of the cannulated modular tibial prosthetic stem component for defining a circumscribing bone kerf around at least the inferior most cannulated modular tibial stem component piece.

11. The system of claim 10 wherein said offset chisel head includes a chisel having an offset portion upwardly and outwardly diverging from an exterior surface of a base of said offset chisel head and a cutting portion upwardly transitioning away from said offset portion in a direction parallel to said cannulated drive shaft.

12. The system of claim 11 wherein said cutting portion has a radius of curvature that matches a radius of curvature of the inferior most cannulated modular tibial stem component piece of the cannulated modular tibial prosthetic stem component disposed within the distal tibia.

13. The system of claim 9 further comprising a circular saw head configured to be disposed within the tibial-talar space and surmounting one end of said cannulated drive shaft for circumferentially cutting bone around at least an inferior most cannulated modular tibial stem component piece of the cannulated modular tibial prosthetic stem component for defining a circumscribing bone kerf around at least the inferior most cannulated modular tibial stem component piece.

14. The system of claim 13 wherein said circular saw head comprises an inferior base transitioning into a cylindrical sidewall defining an interior cavity configured to closely receive at least the inferior most cannulated modular tibial stem component piece of the cannulated modular tibial prosthetic stem component disposed within the distal tibia.

* * * * *